US008821512B2

(12) United States Patent
Barrier et al.

(10) Patent No.: US 8,821,512 B2
(45) Date of Patent: Sep. 2, 2014

(54) MANIPULATOR WITH MANUAL HOLD AND COMFORTABLE ARTICULATION

(75) Inventors: Pascal Barrier, Annecy (FR); Jérémy Ollagnier, Meythet (FR); Rémi Rosset-Lanchet, Annecy (FR)

(73) Assignee: Dexterite Surgical, Annecy (FR)

( * ) Notice: Subject to any disclaimer, the term of this patent is extended or adjusted under 35 U.S.C. 154(b) by 313 days.

(21) Appl. No.: 13/387,782

(22) PCT Filed: Jul. 30, 2010

(86) PCT No.: PCT/IB2010/053475
§ 371 (c)(1),
(2), (4) Date: Jan. 30, 2012

(87) PCT Pub. No.: WO2011/013102
PCT Pub. Date: Feb. 3, 2011

(65) Prior Publication Data
US 2012/0130355 A1    May 24, 2012

(30) Foreign Application Priority Data
Jul. 31, 2009   (FR) ...................................... 09 55383

(51) Int. Cl.
*A61B 19/00* (2006.01)
*A61B 17/00* (2006.01)
*A61B 17/04* (2006.01)
*A61B 17/29* (2006.01)

(52) U.S. Cl.
CPC ......... *A61B 17/2909* (2013.01); *A61B 17/0469* (2013.01); *A61B 2017/2929* (2013.01); *A61B 2019/2269* (2013.01); *A61B 2017/0042* (2013.01); *A61B 2017/291* (2013.01); *A61B 19/22* (2013.01)
USPC ................................ 606/130; 606/1; 606/170

(58) Field of Classification Search
USPC ............ 606/1, 130, 139, 144, 148, 167, 170, 606/180; 600/104, 197
See application file for complete search history.

(56) References Cited

U.S. PATENT DOCUMENTS

| | | | | |
|---|---|---|---|---|
| 5,836,960 | A * | 11/1998 | Kolesa et al. ................. | 606/170 |
| 6,077,286 | A | 6/2000 | Cuschieri | |
| 7,476,226 | B2 * | 1/2009 | Weikel et al. .................... | 606/79 |
| 8,092,373 | B1 * | 1/2012 | Papouras et al. .............. | 600/131 |
| 8,157,817 | B2 * | 4/2012 | Bonadio et al. ............... | 606/148 |
| 8,613,740 | B2 * | 12/2013 | Barrier et al. ..................... | 606/1 |
| 8,696,651 | B2 * | 4/2014 | Barrier et al. ..................... | 606/1 |

(Continued)

FOREIGN PATENT DOCUMENTS

| | | | |
|---|---|---|---|
| DE | 9203041 | U1 | 6/1992 |
| DE | 29623921 | U1 | 9/2000 |
| NL | 1004375 | C2 | 5/1998 |

*Primary Examiner* — Ahmed Farah
(74) *Attorney, Agent, or Firm* — William H. Eilberg (57) ABSTRACT

A manipulator includes a control unit (1), with handle (4) and control buttons (4*a*-4*d*), and a connecting arm (2) which, at its proximal end (2*a*), carries the control unit (1) and, at its distal end (2*b*), carries a work unit (3). The handle (4) is articulated about at least one transverse articulation axis (4*e*), which is itself situated at an intermediate position along the handle (4). A particularly ergonomic manipulator is thus obtained which is easy to learn to use and which efficiently separates the stresses arising from movements of the tool support (5) and the stresses arising from holding and moving the manipulator itself.

10 Claims, 8 Drawing Sheets

(56) References Cited

U.S. PATENT DOCUMENTS

| | | |
|---|---|---|
| 2005/0222587 A1 | 10/2005 | Jinno |
| 2006/0020287 A1 | 1/2006 | Lee |
| 2006/0206101 A1* | 9/2006 | Lee .................................. 606/1 |
| 2008/0287862 A1* | 11/2008 | Weitzner et al. ................ 604/28 |

* cited by examiner

MANIPULATOR WITH MANUAL HOLD AND COMFORTABLE ARTICULATION

TECHNICAL FIELD OF THE INVENTION

The present invention concerns manipulator devices for controlling from outside an operating area the movements of a manipulation instrument situated inside the operating area.

In particular, these manipulator devices are used to place and control a surgical tool in minimally invasive surgical applications employing endoscopy.

In these applications, it is necessary to be able to move and to control a surgical tool to effect diverse operations such as a suture, tightening a knot, fine dissection of tissues. These are delicate, precise operations in which the movements to be carried out are complex.

The invention concerns more specifically portable manipulator devices in which a surgical tool is placed at the end of a manipulator that the surgeon holds in one hand and essentially has a connecting arm with a proximal end and a distal end. The proximal end of the connecting arm includes a control unit having a handle adapted to be held by said hand and including at least one control member adapted to be loaded by at least one finger of said hand holding the handle to actuate the surgical instrument.

There is known from the document U.S. Pat. No. 6,077, 286, for example, one such portable manipulator device in which the handle is a rod provided with a lever extending the entire length of the rod and articulated at its distal end in such manner that the user holding the handle can pivot the lever toward an open position and a closed position while holding the manipulator.

The lever thus constitutes a control member mounted on the handle and adapted to be loaded by at least one finger of the hand holding the handle.

The handle is mounted at the proximal end of a connecting arm that extends along a longitudinal arm axis and that carries at its distal end a working unit carrying a tool. The tool may have jaws, opening and closing of which are commanded by the pivoting of the lever.

The above document proposes to improve the ergonomics of holding and manipulating the handle by providing a connection articulated about a transverse axis between the proximal end of the connecting arm and the distal end of the handle, with means for locking the angular position of the handle. Accordingly, in the above document, the articulation of the handle is at the distal end of the handle and the holding section by which the user holds the handle is entirely in a proximal area relative to the articulation.

In the device of the above prior art document, loading the articulated lever necessarily produces simultaneous loading of the handle, with the result that there is no perfect decoupling between the movement of closing or opening the tool by the rotation of the lever and the positioning of the tool at the end of the connecting arm.

Moreover, when the handle has been pivoted, for improved operator comfort, pulling or pushing the handle to produce an axial movement of the manipulator is eccentric relative to the axis of the connecting arm, which necessarily produces a torque tending to incline the manipulator and unwanted movement of the tool, which the operator must attempt to correct by applying a torque to the handle.

Furthermore, in the pivoted position of the handle, pulling the handle to produce an axial movement of the manipulator necessarily produces unwanted loading of the lever and thus unwanted actuation of the tool.

At the same time, the aim is to improve the ergonomics of the portable manipulator to enable the manipulator to be held and the surgical tool to be loaded in all the desired movements without the operator having to place their hands in limiting or uncomfortable positions of their wrist, elbow and shoulder joint.

The document US 2008/0287862 A1 describes a manipulator comprising:
- a control unit, having a handle adapted to be held in one hand, and having fixing and guiding means for fixing it to a fixed support so as to slide thereon,
- at least one control member, mounted on the handle, and adapted to be loaded by at least one finger of the hand holding the handle,
- a connecting arm, extending along an arm longitudinal axis, having a proximal end in which the control unit is mounted, and having a distal end,
- a working unit, mounted on the distal end of the connecting arm, including a tool support adapted to support a tool, and actuated by said at least one control member,
- the handle being elongate along a handle longitudinal axis and being conformed to be held in the palm of the hand with the thumb opposite the other fingers to surround its lateral surface in a holding section,
- the handle being articulated, in the control unit, with at least one degree of freedom in rotation about a first articulation axis transverse to its handle longitudinal axis,
- the first articulation axis of the handle being in an intermediate position along the handle longitudinal axis, with the result that the holding section extends either side of the first articulation axis of the handle,
- the first articulation axis intersecting the longitudinal axis of the connecting arm.

Thanks to the intermediate position of the first articulation axis of the handle, and thanks to the fact that the articulation axis intersects the longitudinal axis of the connecting arm, the operator holds the handle on either side of the first articulation axis of the handle and axial pulling or pushing movements of the manipulator produce substantially opposite handle rotation torques, reducing any unwanted forces applied laterally to the manipulator in a plane perpendicular to the first articulation axis. However, it is found that there remain unwanted forces in planes non-perpendicular to the first articulation axis, with the result that the accuracy of positioning and driving the tool is not yet sufficient.

Moreover, in the above document, movements of the handle relative to the control unit cause loading of the actuators that move the distal tool relative to the connecting arm. This induces a non-dissociation between positioning the tool and commanding movements of the tool during a surgical operation. To this end, the above document provides for fixing the control unit to a fixed support. The manipulator is not portable.

SUMMARY OF THE INVENTION

The problem addressed by the present invention is further improving the accuracy of the positioning and the driving in movement of a tool by a portable manipulator, avoiding all unwanted movements and ensuring good dissociation between positioning the tool and commanding movements of the tool during a surgical operation.

At the same time, the aim is to facilitate axial rotation of the manipulator about the longitudinal axis of the connecting arm by maneuvering the handle alone, limiting the amplitude of the necessary movements of the wrist, elbow and shoulder of the operator.

To achieve the above and other objects, the longitudinal handle axis also intersects the longitudinal axis of the connecting arm.

As a result, the rotation torques are balanced in all directions about the longitudinal axis of the connecting arm.

Furthermore, the handle is fixed in axial rotation about its longitudinal axis relative to the control unit, and the manipulator has no direct or indirect coupling means with movements of the handle relative to the control unit and movements of the tool support and the tool relative to the connecting arm.

The absence of relative rotation of the handle about its longitudinal axis makes it possible to avoid the impossibility or great difficulty of driving the manipulator in axial rotation when the handle is substantially aligned with the connecting arm.

The absence of any coupling means between relative movements of the handle and relative movements of the tool support enables good dissociation between holding the tool in position and commanding relative movements of the tool, and enables the hand of the operator to hold the handle easily whatever the position of the manipulator, and this despite the physiological limitations of the human hand.

Figure 18:
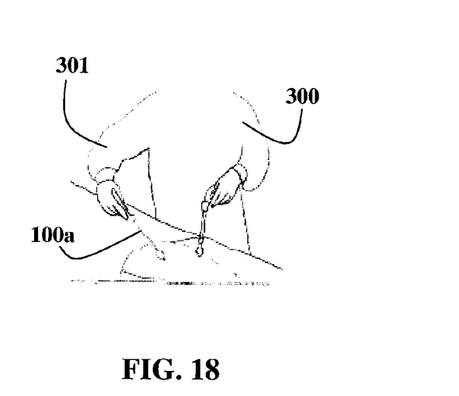
FIGS. 18 and 19 show an ergonomic effect of a manipulator with a positioning arm.

Furthermore, by the combination with the transverse position of the first articulation axis relative to the longitudinal axis of the handle, the amplitude of the necessary movements of the arm of the operator to cause the manipulator to pivot about its longitudinal axis is greatly reduced, in particular in offset positions of the manipulator (FIG. 18).

In the description and the claims the expressions "intersecting" must not be considered in any strict mathematical sense of intersecting straight lines that meet at one point, but rather in a physical, more approximate sense of procuring a sufficient technical effect of dissociation between the different movements of positioning the manipulator. Thus the three axes concerned, namely the first articulation axis, the handle longitudinal axis and the longitudinal axis of the connecting arm are considered to "intersect" if they all three intersect a 15 mm diameter sphere. As a result, the lever arms are sufficiently short for the unwanted torques induced by the different movements to be negligible. It is also considered that intersecting axes may coincide (i.e. be superposed) in certain positions.

A further improvement is obtained by providing that the first articulation axis is in a balanced intermediate position along the holding section of the handle. This ensures that the rotation torques applied to the handle when pulling or pushing axially or when rotating the handle about the first axis are exactly compensated, preventing any lateral loading on the manipulator and consequently preventing any unwanted movement of the tool.

The control members are preferably disposed on the handle remotely from the bearing areas of the holding section. In other words, the control members are placed on the handle so that they are loaded by a part of the hand that is not used for holding the manipulator. This further reduces the risk of interference between the movements of positioning the tool and the movements of actuating the tool.

To increase also the movement capacities of the handle, there may be provision for the handle additionally to be articulated in the control unit with a second degree of freedom in rotation about a second articulation axis.

The articulation axes could advantageously intersect with the longitudinal axis of the arm.

In a first embodiment, the handle is free to pivot in the control unit.

In a second embodiment, means may further be provided for locking the handle against rotation about the articulation axis or axes, thereby giving the operator a few additional possibilities for holding the manipulator if the connecting arm is badly guided or not guided in a trocar.

A simpler structure may nevertheless be preferred in which the handle is articulated with only one degree of freedom in rotation, about the first articulation axis. It is easier to learn to use such a structure to achieve correct positioning of the tool in the operating cavity and prevent unwanted movements.

In this case, it will be advantageous for the first articulation axis to be oblique to the longitudinal axis of the connecting arm: this oblique orientation better overcomes the physiological limitations of the human hand when rotating the manipulator about the longitudinal axis of the connecting arm.

In another embodiment there is provided between the articulation of the handle and the control body a positioning arm by means of which the operator may modify and fix the relative spatial and/or angular position of the first articulation axis of the handle in the control unit.

This positioning arm may be a semi-rigid rod 5 to 30 cm long, deformable under flexing or twisting forces greater than the forces produced only by the weight of the manipulator and the resistance of the tissues treated by the manipulator. As a result, the operator may hold the manipulator without the deformable arm being deformed and may deform the arm at will by more intense loading using both hands. The operator may thus place the articulation axis of the handle in any space, at will, for improved handling and improved comfort of the elbow and/or the shoulder of the operator.

Alternatively, the positioning arm may be a rod carrying at its proximal end the first articulation axis of the handle and articulated at its distal end on the connecting arm or a control body by an articulation that may be locked.

The presence of such a positioning arm in reality enables the operator, within a wide range of possibilities, to modify and fix the position and the orientation of the handle relative to the connecting arm and to the rest of the manipulator. The operator may thus conform the manipulator, before effecting an operative gesture, to impart to it a shape better suited to the gesture that they must make, so as to make the gesture without having to place their hand in limiting or uncomfortable positions of their wrist, elbow or shoulder joint. Such a result may be achieved independently of the presence or the absence of a handle articulation.

The presence of such a positioning arm between the handle and the connecting arm constitutes an independent invention.

The invention applies with advantage to the situation in which actuation of a first command member commands an inclination actuator housed in a control body that drives an inclination movement of the tool support.

BRIEF DESCRIPTION OF THE DRAWINGS

Other objects, features and advantages of the present invention will emerge from the following description of particular embodiments given with reference to the appended figures, in which.

DESCRIPTION OF PREFERRED EMBODIMENTS

Figure 1:
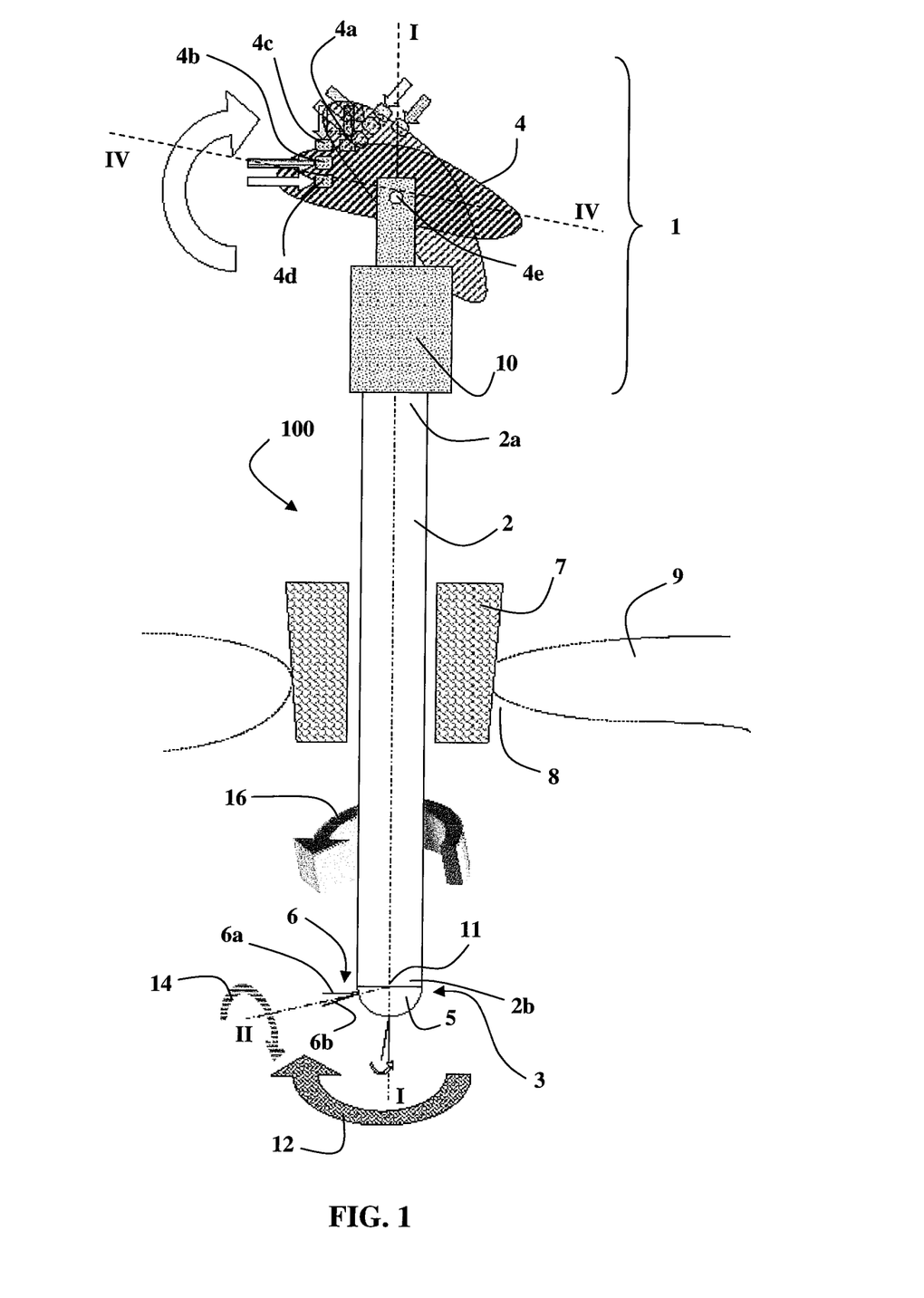
FIG. 1 is a diagrammatic general view showing a manipulator of one embodiment of the present invention in the position of use for a surgical operation.

Consider firstly the general structure of a manipulator of the invention, as illustrated by the FIG. 1 embodiment.

In this embodiment, the manipulator 100 comprises a control unit 1, a connecting arm 2 that extends along a longitudinal axis I-I of the connecting arm, and a working unit 3.

The control unit 1 is mounted on the proximal end 2a of the connecting arm 2 and the working unit 3 is mounted on the distal end 2b of the connecting arm 2.

The control unit 1 comprises a handle 4 adapted to be held by one hand of an operator and a control body 10 containing various driving means for producing the appropriate movements in the working unit 3.

The control unit 1 is preferably balanced about the longitudinal axis I-I of the connecting arm, i.e. its center of gravity is substantially centered on said longitudinal axis I-I of the connecting arm.

The working unit 3 includes a tool support 5 adapted to support a tool 6. The figure shows by way of example a tool 6 in the form of forceps with two branches 6a and 6b. Other forms of tool are naturally possible, for example a simple hook.

The handle 4 includes at least one control member. In the example described, the handle 4 includes a first control member 4a, a second control member 4b, a third control member 4c, and a forceps control member 4d.

As in known devices, the connecting arm 2 passes through a trocar 7 providing the connection and the entry into an opening 8 produced in the body wall 9 of a patient. The control unit 1 remains outside the body of the patient, while the working unit 3 penetrates to the interior of the body of the patient to reach the operating area where the tool 6 must execute movements controlled from the control unit 1.

In the embodiment shown in FIG. 1, the tool support 5 and the tool 6 may be actuated from the control unit 1 to effect one or more movements.

For example, loading the first control member 4a of the handle 4 commands an inclination actuator accommodated in the control body 10 which itself drives the tool support 5 in a movement 12 of inclination about a transverse inclination axis 11. Thus the tool support 5 and the tool 6 may assume an inclination in which they are oriented in an inclination direction II.

Loading the second control member 4b of the handle 4 commands a rotation actuator accommodated in the control body 10 that drives the tool support 5 in a rotation movement 14 about the direction of inclination II.

Loading the third control member 4c of the handle 4 commands an arm rotation actuator accommodated in the control body 10 that produces a movement 16 of orientation whereby the inclination direction II is oriented about the longitudinal axis I-I of the connecting arm 2.

Actuating the forceps control member 4d of the handle 4 controls a forceps actuator to obtain either the opening or the closing of the forceps 6.

Each of the actuators may be of electric motor, hydraulic or pneumatic actuator, or mechanical transmission type. Electric motor actuators may be preferred, notably for simplicity of power supply and flexibility of operation and control.

The handle 4 includes a body elongate along a longitudinal handle axis IV-IV and is articulated in the control unit 1 about a first articulation axis 4e.

Figure 2:
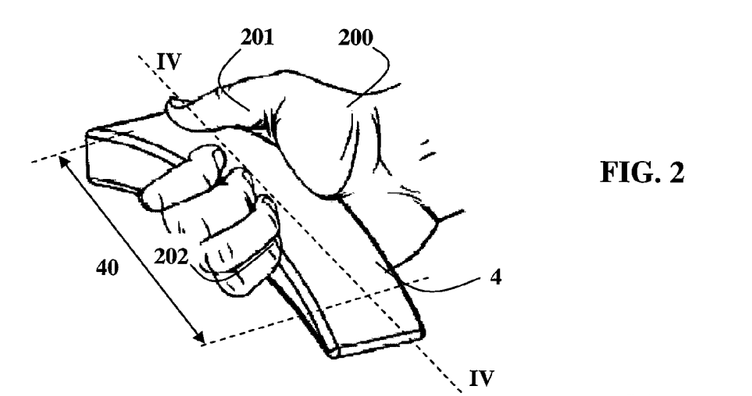
FIGS. 2, 3 and 4 are views in perspective showing a hand holding a handle of the manipulator from FIG. 1.
Figure 3:
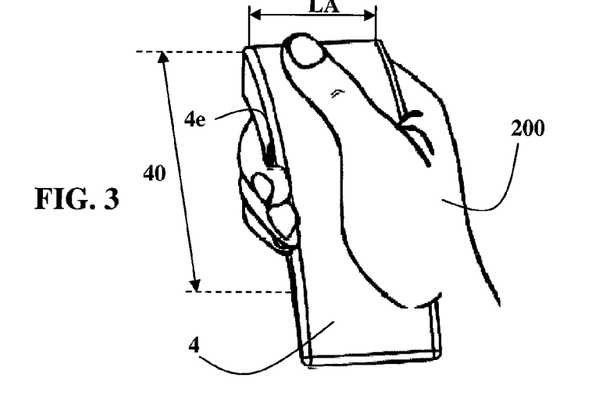
Figure 4:
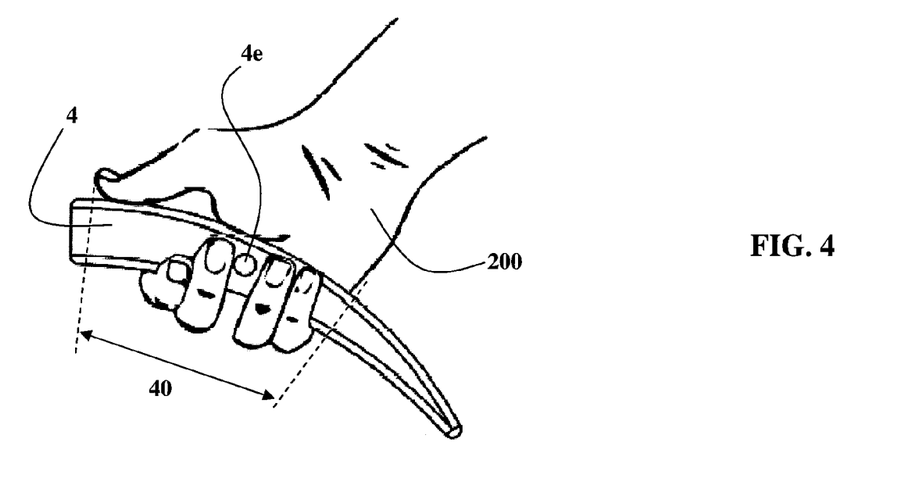

Consider now FIGS. 2 to 4. The handle 4 is shown in a slightly different form from that of FIG. 1, but still constituting a handle body elongate along a longitudinal handle axis IV-IV. A hand 200 is positioned normally on the handle with the thumb on the opposite side to the other fingers to surround the lateral surface of the handle in a holding section 40. In practice, the handle 4 has a width LA (FIG. 3) sufficiently small for the handle 4 to be held in the palm of one hand 200, with the thumb 201 opposite the other fingers 202 to surround its lateral surface in the holding section 40. The length of the holding section 40 is approximately 10 cm.

The handle 4 is articulated in the control unit 1 about a first articulation axis 4e transverse to its longitudinal handle axis IV-IV.

FIGS. 3 and 4 show the position of the transverse first articulation axis 4e along the handle longitudinal axis IV-IV.

As may be seen, the first articulation axis 4e of the handle 4 is in an intermediate position along the handle longitudinal axis IV-IV with the result that the holding section 40 lies on either side of the first articulation axis 4e of the handle 4. In the embodiment shown in FIGS. 2 to 4, the first articulation axis 4e is in reality at a balanced intermediate position along the holding section 40 of the handle 4, i.e. the first articulation axis 4e is substantially halfway along the holding section 40.

Figure 5:
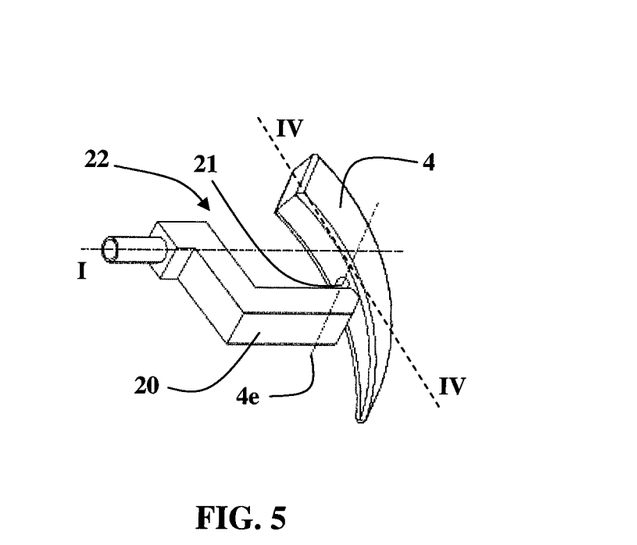
FIGS. 5 and 6 are perspective views showing the articulation of a manipulator handle of a first embodiment of the invention.
Figure 6:
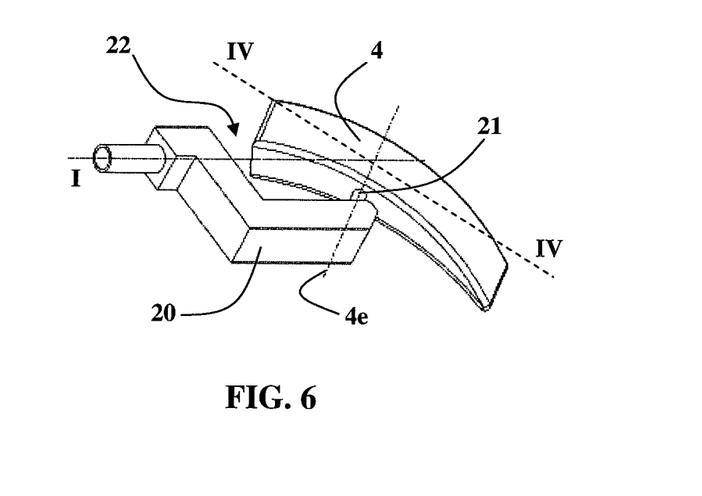
Figure 7:
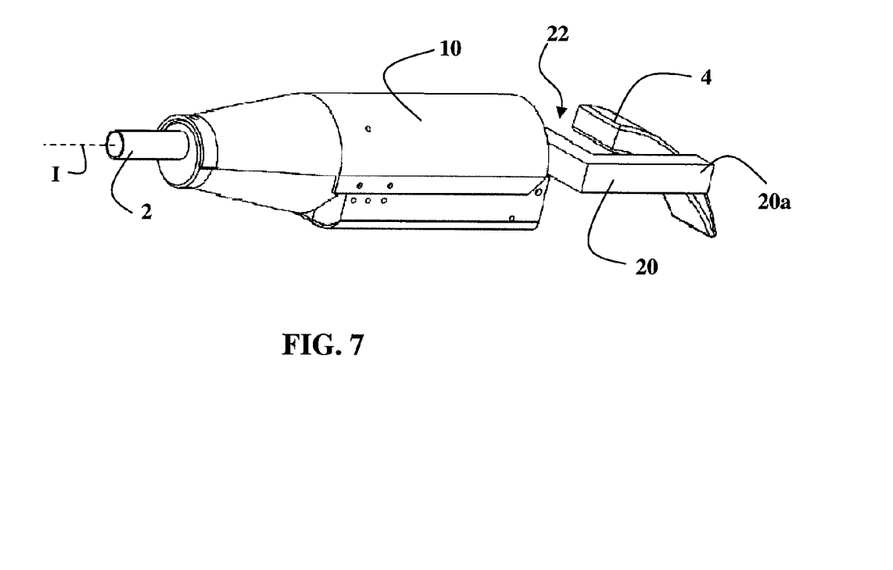
FIGS. 7 to 10 show in perspective a manipulator handle articulation of a second embodiment of the present invention, in four successive positions during axial rotation of the manipulator.
Figure 8:
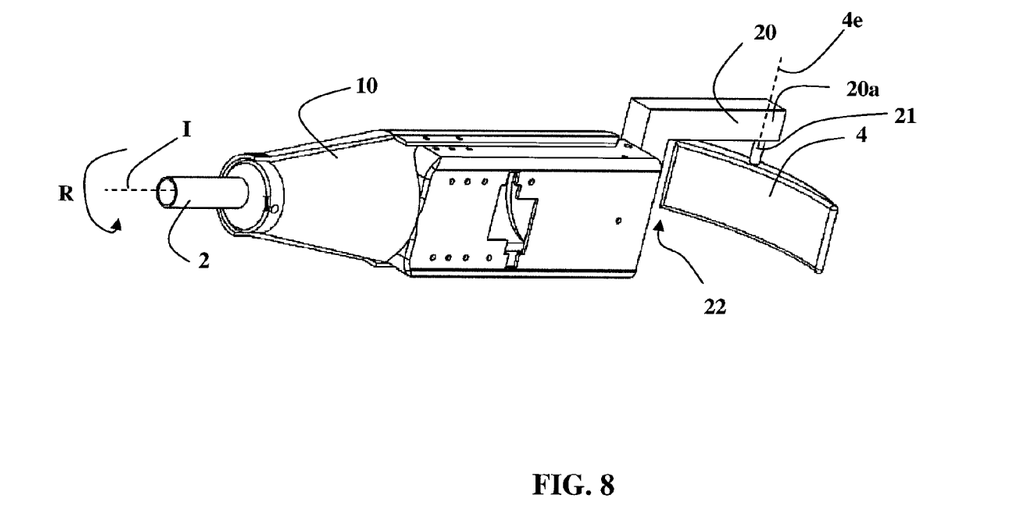
Figure 9:
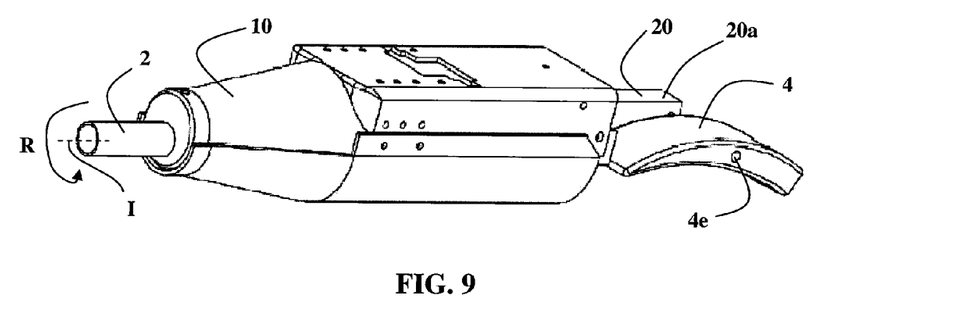
Figure 10:
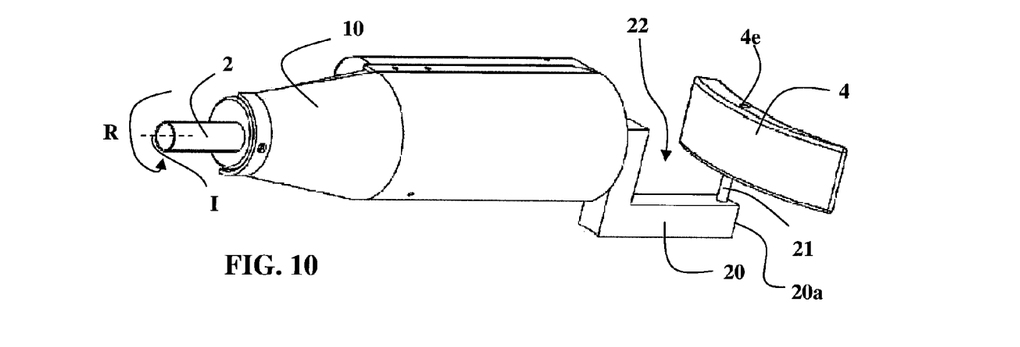

Consider now a first embodiment of the articulation of the handle 4 in the control unit as shown in FIGS. 5 and 6.

These figures show the arm longitudinal axis I-I, the handle longitudinal axis IV-IV, and the first articulation axis 4e. The first articulation axis 4e intersects the longitudinal axis I-I of the connecting arm 2 and is oblique relative to said longitudinal axis I-I of the connecting arm 2.

Similarly, the handle longitudinal axis IV-IV intersects the longitudinal axis I-I of the connecting arm 2.

In the embodiment shown in FIGS. 7 to 10, the first articulation axis 4e is substantially perpendicular to the longitudinal axis I-I of the connecting arm 2.

Figure 11:
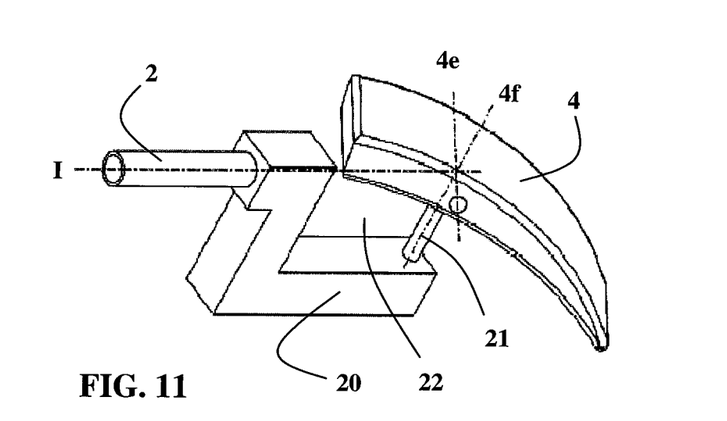
FIGS. 11, 12 and 13 show a manipulator handle articulation of a third embodiment of the present invention.
Figure 12:
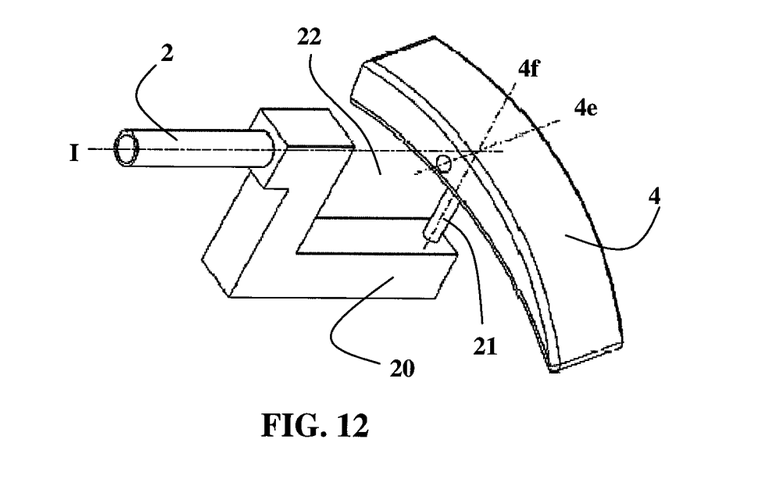
Figure 13:
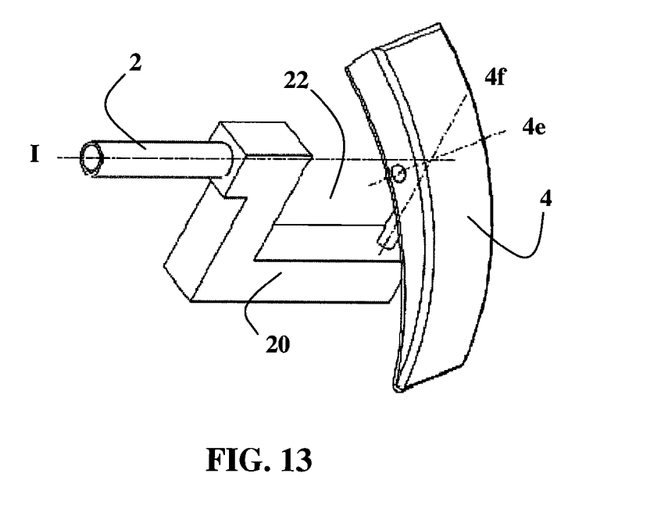

In the embodiment shown in FIGS. 11 to 13, the handle 4 is articulated about two articulation axes 4e and 4f that are perpendicular to and intersect the longitudinal axis I-I of the connecting arm 2.

In all the embodiments of FIGS. 5 to 13, the control unit 1 comprises a longitudinal proximal arm 20, offset laterally, away from the longitudinal axis I-I of the connecting arm 2, and carrying at its proximal end 20a a transverse arm 21 to which the handle 4 is articulated. The arms 20 and 21 define a free space 22 around the handle 4 providing a free passage for the fingers of the hand holding the handle during movements thereof about the first articulation axis 4e.

Clearly the capacity for pivoting of the handle 4 enables the handle to be held in positions limiting the angulation of the wrist joint of the hand of the user whilst giving the manipulator different orientations that correspond to the desired position of the tool 6.

Manipulation of the control members 4a-4d enables actuation of the tool support 5 and the tool 6 without affecting the holding of the manipulator by the handle 4, thus ensuring good decoupling between holding the manipulator and actuation of the tool 6 and the tool support 5.

FIGS. 7 to 10 show an interesting effect of the articulated and balanced handle of the invention, namely commanding axial rotation R of the manipulator exclusively by the rotation torques applied by the hand of the operator holding the handle 4, without the thumb and the opposite fingers leaving the handle. Because the control unit 1 is balanced about the arm longitudinal axis I-I, the axial rotation R is regular and controlled perfectly merely by maneuvering the handle 4 by which the hand of the operator simultaneously holds the manipulator.

The movements of the handle 4 relative to the control unit 1 to effect the axial rotation R do not affect the relative position of the tool 6 and/or the tool support 5 relative to the connecting arm 2.

In all the embodiments that have been described, there may further be provided means for locking the handle 4 against rotation about the articulation axis or axes 4e. This locking may be effected by any means known to the person skilled in the art, for example by clamping means about the articulation axis 4e.

Figure 14:
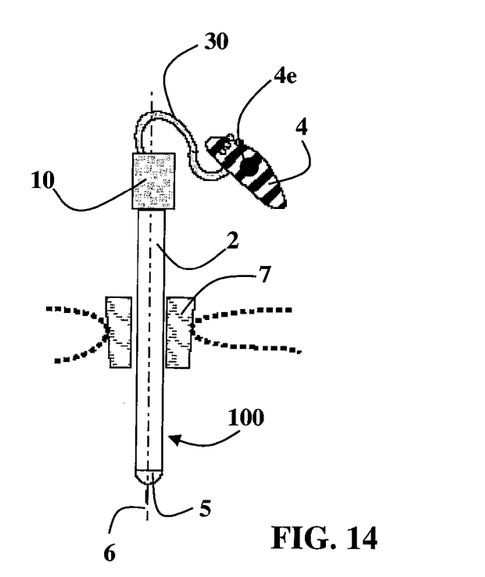
FIG. 14 shows in side view a manipulator having a deformable positioning arm and an articulated handle.

Consider next FIG. 14, which shows a manipulator in which a positioning arm 30 is provided between the articulation 4e of the handle 4 and the control body 10.

In this embodiment, the positioning arm 30 is a semi-rigid rod 5 to 30 cm long, deformable by bending or twisting forces greater than the forces produced by the weight of the manipulator 100 and the resistance of the tissues treated by the manipulator 100.

In practice, for a manipulator having a mass of approximately 0.5 kg, a semi-rigid rod is provided that is deformable by a force from 10 to 50 N and which then retains its shape. As a result, the user may hold the manipulator 100 by the handle 4 without deforming the arm 30.

Thanks to the capacity for deformation of the positioning arm 30 by higher forces, the user may conform the arm so as to impart to it a shape enabling holding of the handle 4 in all desired positions, for example an offset position. This reduces fatigue of the wrist, elbow and shoulder of the operator in some operating conditions in which the manipulator 100 must be offset away from the body of the operator.

The deformation and the locking in shape of the positioning arm 30 may be effected using hydraulic, pneumatic or mechanical forces, including friction. By way of example, the deformable positioning arm 30 may be a multiply articulated rod having a plurality of segments articulated to each other, each articulation being braked by friction members, possibly with indexing means.

Figure 16:
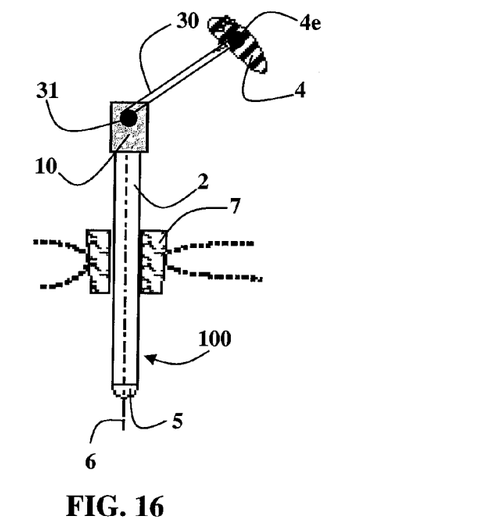
FIG. 16 shows a variant manipulator with an articulated positioning arm and an articulated handle.

FIG. 16 shows a variant in which the positioning arm 30 is a rigid rod articulated to the control body 10 or to the connecting arm 2 by an articulation 31 with a transverse axis provided with braking or indexing means. For example, the articulation comprises at least two corrugated washers applied axially one against the other by spring means and the corrugations of which tend to interengage one on the other. The handle 4 is articulated about a first articulation axis 4e at the end of the positioning arm 30.

A first independent invention may consist in the use of a positioning arm of the semi-rigid rod type as described above in relation to FIG. 14, which gives a great capacity for modification of the positioning and the orientation of a handle relative to the rest of the manipulator. The handle 4 is articulated to the end of the positioning arm 30.

Figure 15:
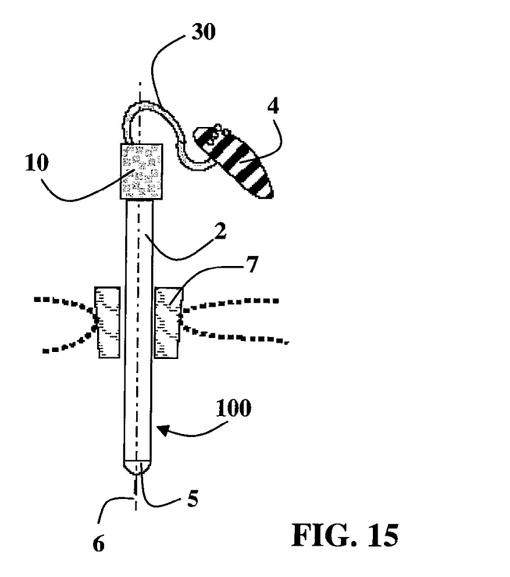
FIG. 15 shows a manipulator with a deformable positioning arm and a fixed handle.

FIG. 15 shows another possibility, in which the handle 4 is fixed to the end of a positioning arm 30 of semi-rigid rod type that connects it to the control body 10 and to the connecting arm 2 the distal end of which carries the tool support 5 and the tool 6.

A second independent invention may consist in the use of a positioning arm of the rigid rod type articulated to the end of the connecting arm, as described above with reference to FIG. 16. In this case, ergonomic considerations necessitate the provision of at least one control member mounted on the handle and commanding an actuator that drives the tool support 5 with a movement of inclination relative to the longitudinal axis of the connecting arm 2.

Figure 17:
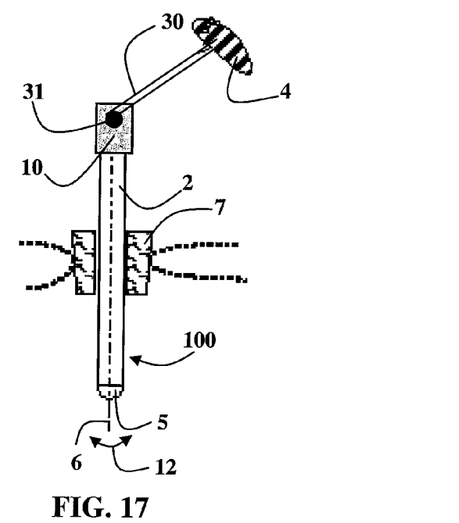
FIG. 17 shows a manipulator with an articulated positioning arm and a fixed handle.

FIG. 17 shows another possibility, in which the handle 4 is fixed to the end of the positioning arm 30 of articulated rigid rod type and movement in orientation 12 of the tool support 5 is controlled by one of the control members 4a of the handle 4.

Otherwise, these devices from FIGS. 14 to 17 may employ the means previously described with reference to FIG. 1.

Figure 19:
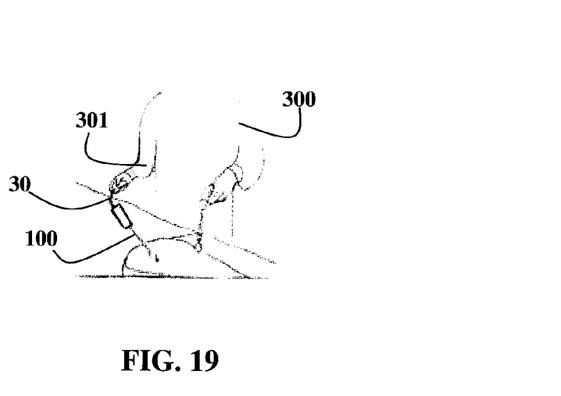

FIGS. 18 and 19 show the ergonomic effect of the presence of a positioning arm 30 in the case of manipulation of the manipulator in an eccentric position: see in FIG. 18 the offset and tiring position of the right arm 301 of the operator 300 holding a prior art manipulator 100a, and see in FIG. 19 the natural close and comfortable position of the right arm 301 of the operator 300 who is holding a manipulator 100 with a positioning arm 30 of the invention.

The present invention is not limited to the embodiments explicitly described but includes the diverse variants and generalizations thereof contained within the scope of the following claims.

The invention claimed is:

1. Manipulator comprising:
    a control unit (1), having a handle (4) adapted to be held in one hand,
    at least one control member (4a-4d), mounted on the handle (4), and adapted to be loaded by at least one finger of the hand holding the handle (4),
    a connecting arm (2), extending along an arm longitudinal axis (I-I), having a proximal end (2a) in which the control unit (1) is mounted, and having a distal end (2b),
    a working unit (3), mounted on the distal end (2b) of the connecting arm (2), including a tool support (5) adapted to support a tool (6), and actuated by said at least one control member (4a-4d),
        the handle (4) being elongate along a handle longitudinal axis (IV-IV) and being conformed to be held in the palm of the hand (200) with the thumb (201) opposite the other fingers (202) to surround its lateral surface in a holding section (40),
    the handle (4) being articulated, in the control unit (1), with at least one degree of freedom in rotation about a first articulation axis (4e) transverse to its handle longitudinal axis (IV-IV),
    the first articulation axis (4e) of the handle (4) being in an intermediate position along the handle longitudinal axis (IV-IV), with the result that the holding section (40) extends either side of the first articulation axis (4e) of the handle (4),
    the first articulation axis (4e) intersecting the longitudinal axis (I-I) of the connecting arm (2), wherein:
the handle longitudinal axis (IV-IV) intersects the longitudinal axis (I-I) of the connecting arm (2),
the handle (4) is fixed against axial rotation about its longitudinal axis (IV-IV) relative to the control unit (1),
the manipulator has no direct or indirect coupling means between the movements of the handle (4) relative to the control unit (1) and the movements of the tool support (5) and the tool (6) relative to the connecting arm (2).

2. Manipulator according to claim 1, wherein the first articulation axis (4e) is in a balanced intermediate position along the holding section (40) of the handle (4).

3. Manipulator according to claim 1, wherein the handle (4) is furthermore articulated in the control unit (1) with a second degree of freedom in rotation about a second articulation axis (4f).

4. Manipulator according to claim 3, wherein the articulation axes (4e, 4f) intersect the longitudinal axis (I-I) of the arm (2).

5. Manipulator according to claim 1, wherein it further comprises means for locking the handle (4) against rotation about the first articulation axis (4e).

6. Manipulator according to claim 1, wherein actuation of a first control member (4a) commands an inclination actuator accommodated in a control body (10) that drives the tool support (5) in an inclination movement (12).

7. Manipulator according to claim 1, wherein the handle (4) is articulated with only one degree of freedom in rotation about the first articulation axis (4e).

8. Manipulator according to claim 7, wherein the first articulation axis (4e) is oblique relative to the longitudinal axis (I-I) of the connecting arm (2).

9. Manipulator according to claim 1, wherein the center of gravity of the control unit (1) is substantially centered on the arm longitudinal axis (I-I).

10. Manipulator according to claim 1, wherein the handle (4) is furthermore articulated in the control unit (1) with a second degree of freedom in rotation about a second articulation axis (4f), and wherein it further comprises means for locking the handle (4) against rotation about the first and second articulation axes (4e, 4f).

* * * * *